United States Patent
Hyoda et al.

(10) Patent No.: US 7,122,676 B2
(45) Date of Patent: Oct. 17, 2006

(54) PROCESS FOR THE PREPARATION OF 5,5'-BI-1H-TETRAZOLEDIAMMONIUM SALTS USING HYDRAZINE HYDRATE AND DICYAN AS STARTING MATERIALS

(75) Inventors: Shunji Hyoda, Sakaide (JP); Masaharu Kita, Sakaide (JP); Hirotoshi Sawada, Sakaide (JP); Shuichi Nemugaki, Sakaide (JP); Takahiro Ueta, Sakaide (JP); Kohki Satoh, Sakaide (JP)

(73) Assignees: Japan Hydrazine Co., Ltd., Tokyo (JP); Masuda Chemical Industries Co., Ltd., Kagawa-Ken (JP)

( * ) Notice: Subject to any disclaimer, the term of this patent is extended or adjusted under 35 U.S.C. 154(b) by 1088 days.

(21) Appl. No.: 09/813,826

(22) Filed: Mar. 22, 2001

(65) Prior Publication Data

US 2001/0029301 A1    Oct. 11, 2001

(30) Foreign Application Priority Data

Mar. 24, 2000  (JP) ............................. 2000-083714

(51) Int. Cl.
C07D 257/04  (2006.01)
B01J 19/00    (2006.01)

(52) U.S. Cl. ............................. 548/250; 548/250; 516/1
(58) Field of Classification Search .............. 548/250; 516/1

See application file for complete search history.

(56) References Cited

U.S. PATENT DOCUMENTS 6,156,906 A * 12/2000 Hyoda et al. ............... 548/250

FOREIGN PATENT DOCUMENTS

DE       952811       * 11/1956
EP       0 711 762     5/1996
EP       1 016 662     7/2000
EP       1035118 A1   * 9/2000

OTHER PUBLICATIONS

Brotherton, et al. The Synthesis and Chemistry of Cyanogen, Chemical Reviews, U.S., American Chemical Society, Washington, D.C., vol. 59, 1959, pp. 841-883.

Dedichen, Oxalhydrazidine and some heterocyclic complexes, Chemical Abstracts, vol. 31, No. 14, Jul. 20, 1937, Columbus, Ohio, Abstract No. 49878.

Curtius, et al., Mittheilungen Aus Dem Chemischen Institute Der Universitaet Kiels, 19. Synthesen von Benzolhydrazinen mittels Hydrazinhydrat, Journal fuer Praktische Chemie, Leipzig, DE, vol. 50, 1894, pp. 241-274.

Angelli, "Notizie Diverse" Gazzetta Chimica Italiana, Societa Chimica Italiana, Rome, IT, vol. 23, No. 11, 1983, pp. 101-104.

* cited by examiner

Primary Examiner—Joseph K. McKane
Assistant Examiner—Janet L Coppins
(74) Attorney, Agent, or Firm—Sherman & Associates

(57) ABSTRACT

A process for preparing 5,5'-bi-1H-tetrazolediammonium salts (BHT.2NH$_3$) maintaining a high yield through oxaldiimidic acid dihydrazide (OAH) from the starting materials which are cheaply available and are easy to handle. The 5,5'-bi-1H-tetrazolediammonium salts (BHT.2NH$_3$) are prepared by dissolving the oxaldiimidic acid dihydrazide (OAH) obtained by the reaction of hydrated hydrazide with dicyan in an aqueous solution of a weakly acidic compound such as acetic acid, dropwisely adding an aqueous solution of sodium nitrite thereto to form an azide thereof and to effect the cyclization reaction by heating, adding an aqueous solution of sodium hydroxide to the reaction product to convert it into a 5,5'-bi-1H-tetrazoledisodium salt (BHT.2Na), reacting it with an aqueous solution of ammonium chloride, and recovering the formed ammonium salt as sparingly soluble crystals.

13 Claims, No Drawings

PROCESS FOR THE PREPARATION OF 5,5'-BI-1H-TETRAZOLEDIAMMONIUM SALTS USING HYDRAZINE HYDRATE AND DICYAN AS STARTING MATERIALS

BACKGROUND OF THE INVENTION

1. Field of the Invention

The present invention relates to a process for the preparation of 5,5'-bi-1H-tetrazolediammonium salts which are lowly toxic, easy to handle, and are useful as gas-generating agents for air bags and as high-molecular foaming agents.

2. Prior Art

An oxaldiimidic acid dihydrazide has a chemical structure expressed by the following formula (1),

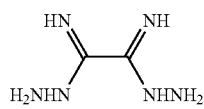
(1)

A 5,5'-bi-1H-tetrazole (BHT) or a salt thereof has a chemical structure expressed by the following formula (2),

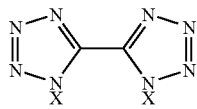
(2)

wherein X is a hydrogen atom or a pair of cations.

The following prior arts 1 to 7 have been known for synthesizing these compounds.

(Prior Art 1) Chemical Abstracts Vol. 31, 4985.

This literature describes the synthesis of a 5,5'-bi-1H-tetrazole (BHT) through an oxaldiimidic acid dihydrazide (OAH) by a reaction expressed by the following formula (3),

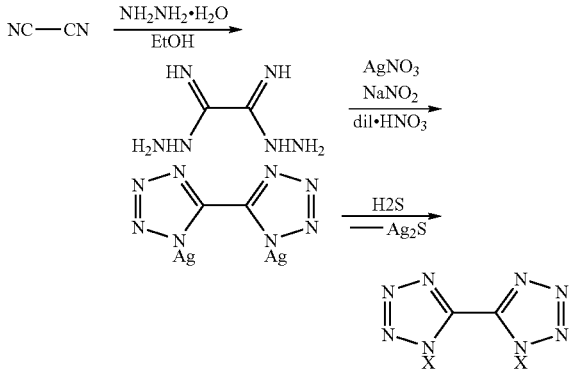
(3)

(Prior Art 2) Journal of Industrial Chemistry Vol. 11, 197–200, (1966).

This literature describes the synthesis of an oxaldiimidic acid dihydrazide (OAH) through an oxaldiimidic acid dimethyl ester intermediate product by a reaction expressed by the following formula (4),

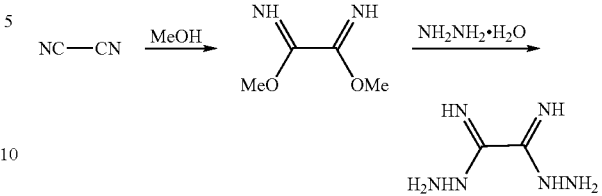
(4)

(Prior Art 3) Friedlich DE952,811 (1956).

This literature describes the preparation of a bitetrazole by the reaction of a mole of sodium azide or hydrogen azide with two moles of sodium cyanide or hydrogen cyanide. Its Example teaches the recovery of a 5,5'-bi-1H-tetrazolediso-dium salt (BHT.2Na) by condensing the solution after the reaction.

This reaction is expressed by the following formula (5),

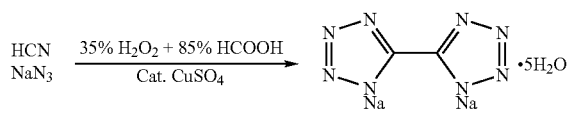
(5)

(Prior Art 4) Friedlich DE952,811 (1956), U.S. Pat. No. 2,710,297, (1955).

This is the same as the above literature. By using manganese dioxide as an oxidizing agent, there is synthesized a 5,5'-bi-1H-tetrazoledisodium salt (BHT.2Na).

This reaction is expressed by the following formula (6),

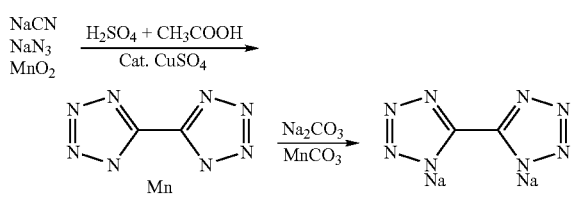
(6)

(Prior Art 5) Feinberg, J. Org. Chem., 29 (1954) 2021.

There has been described the synthesis of a 5,5'-bi-1H-tetrazolediammonium salt (BHT.2NH$_3$) by a reaction expressed by the following formula (7),

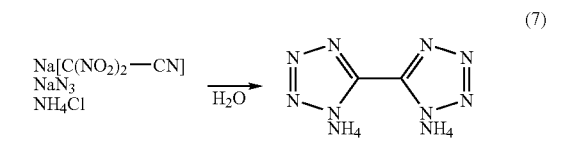
(7)

(Prior Art 6) Japanese Patent Application No. 10-374187

The present inventors have proposed the synthesis of a 5,5'-bi-1H-tetrazolediammonium salt (BHT.2NH$_3$) from hydrogen cyanide, sodium azide and hydrogen peroxide water by a reaction expressed by the following formula (8),

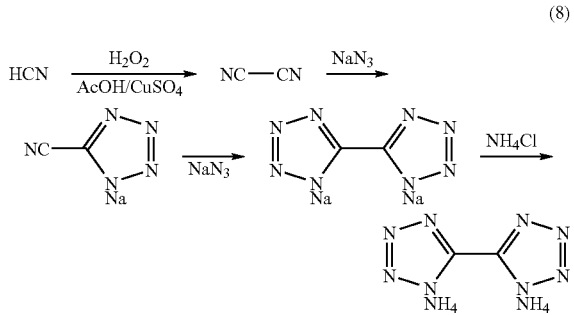

(8)

in the presence of a catalytic amount of copper sulfate while adjusting the pH of the reaction solution to be 5 to 6.

(Prior Art 7) Japanese Patent Application No. 65453/1999.

The present inventors have already proposed the synthesis of a 5,5'-bi-1H-tetrazolediammonium salt (BHT.2NH$_3$) from dicyan and an aqueous solution of sodium azide/ammonium chloride by a reaction expressed by the following formula (9),

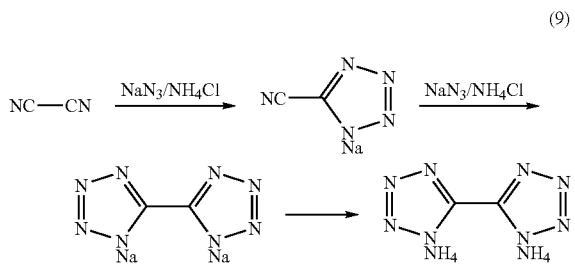

(9)

According to the prior art 1, two moles of hydrazine hydrate and a mole of dicyan are reacted together in a 50% alcohol aqueous solution, and an oxaldiimidic acid dihydrazide is isolated. The prior art 1, however, is silent concerning the reaction conditions, yields or contents. A trace experiment of the examples showed that the yield of the oxaldiimidic acid dihydrazide was as very low as 44.4%, an unstable intermediate product of 1-cyanoformimidic acid hydrazide, that could become a cause of coloring, remained in the isolated crystals of oxaldiimidic acid dihydrazide and, besides, the content was not enough.

According to this method, next, a 5,5'-bi-1H-tetrazoledisilver salt (BHT.2Ag) is isolated under an acidic condition of nitric acid through the formation of an azide thereof and through the cyclization reaction, followed by the reaction with hydrogen sulfide to remove the product as a silver sulfide out of the reaction system, thereby to obtain 5,5'-bi-1H-tetrazole.

This method, however, needs complex steps and uses an expensive silver salt and toxic hydrogen sulfide, which are drawbacks. A trace experiment of the examples was conducted to isolate the 5,5'-bi-1H-tetrazolediammonium salt (BHT.2NH$_3$). However, the yield of the 5,5'-bi-1H-tetrazolediammonium salt (BHT.2NH$_3$) was as very low as 48.7% on the basis of the oxaldiimidic acid dihydrazide.

According to the prior art 2, a dicyan gas is blown into methanol so as to be reacted therewith in the presence of a sodium methylate catalyst to synthesize an oxaldiimidic acid dimethyl ester and, then, the hydrolyzed hydrazine is reacted with the oxaldiimidic acid dimethyl ester in an ethanol solution, in order to isolate the precipitated oxaldiimidic acid dihydrazide crystals.

At the time of synthesizing the oxaldiimidic acid dimethyl ester which is the intermediate product, however, it becomes necessary to isolate the oxaldiimidic acid dimethyl ester which is the intermediate product by distillation after the insoluble matters precipitated from the reaction solution have been isolated by filtration and to react it with the hydrazine hydrate. Thus, the oxaldiimidic acid dihydrazide is prepared through a long step requiring a cumbersome operation, which is a drawback.

The prior art 3 teaches a method of synthesizing and isolating a 5,5'-bi-1H-tetrazoledisoium salt by using hydrogen cyanide and sodium azide as starting materials. Since the 5,5'-bi-tetrazoledisoium salt is soluble in water, an after-treatment such as condensation is necessary for isolating the compound from the aqueous solution, which is a drawback. The prior art 3 describes that the compound was isolated from the aqueous solution through the after-treatment such as condensation of the 5,5'-bi-1H-tetrazoledisodium salt without, however, teaching yields or physical properties of the isolated compound. A trace experiment of the examples showed an yield of as very low as about 30%.

According to the prior art 4, a 5,5'-bi-1H-tetrazoledisodium salt is synthesized by using sodium cyanide, sodium azide and manganese dioxide as an oxidizing agent and by being cyclized with sodium azide. However, since manganese dioxide is used as an oxidizing agent, a cumbersome after-treatment is required for removing it, which is a drawback.

According to the prior art 5, a 5,5'-bi-1H-tetrazolediammonium salt is isolated by using sodium dinitroacetonitrile, sodium azide and ammonium chloride as starting materials. However, there remain such drawbacks as that the reaction time is long, the yield is low and, besides, the dinitroacetonitrile sodium which is the starting material is not easily available.

Prior arts 6 and 7 involve such a drawback that an expensive sodium azide must be used.

SUMMARY OF THE INVENTION

It is therefore an object of the present invention to provide an industrially and economically advantageous process for the preparation of a 5,5'-bi-1H-tetrazolediammonium salt enabling the 5,5'-bi-1H-tetrazolediammonium salt to be obtained in high yields through a very simple operation of synthesizing the 5,5'-bi-1H-tetrazolediammonium salt by using inexpensive and easy-to-handle starting materials through the formation of an oxaldiimidic acid dihydrazide intermediate product, formation of azide and through the cyclization reaction, followed by isolation by filtering after the reaction.

According to the present invention, there is provided a process for the preparation of a 5,5'-bi-1H-tetrazolediammonium salt (BHT.2NH$_3$) by isolating, as crystals, an oxaldiimidic acid dihydrazide (OAH) formed by the reaction of a dicyan with hydrazine hydrate, dissolving the above compound in a weakly acidic aqueous solution, forming an azide thereof with an aqueous solution of sodium nitrite, effecting the cyclization reaction by heating the reaction solution, adding an aqueous solution of sodium hydroxide to the reaction product to convert it into a 5,5'-bi-1H-tetrazoledisodium salt (BHT.2Na), followed by the reaction with ammonium chloride or an aqueous solution of ammonium chloride and recovering the formed ammonium salt as sparingly soluble crystals.

According to the present invention, the 5,5'-bi-1H-tetrazolediammonium salt (BHT.2NH$_3$) is prepared by a combination of the steps of:

1) adding a dicyan to an aqueous solution containing a hydrazine hydrate in an amount larger than a stoichiometric ratio to the dicyan or adding the dicyan to an alcohol/water mixed solution, reacting them with stirring at a temperature lower than room temperature, followed by cooling to isolate the precipitated oxaldiimidic acid dihydrazide (OAH) as crystals maintaining a high purity and a high yield; and 2) dissolving the intermediate product (OAH) in a weakly acidic aqueous solution of a pH of 4 to 6, adding an aqueous solution of sodium nitride thereto to form an azide thereof and to effect the cyclization reaction by heating, adding an aqueous solution of sodium hydroxide to the reaction product to convert it into a 5,5'-bi-1H-tetrazoledisodium salt (BHT.2Na), reacting it with ammonium chloride or an aqueous solution of ammonium chloride, and recovering the formed 5,5'-bi-1H-tetrazolediammonium salt (BHT.2NH$_3$) as sparingly soluble crystals.

The reaction mechanism according to the present invention is in no way limited thereto only but is considered to proceed as expressed by the following formula (10),

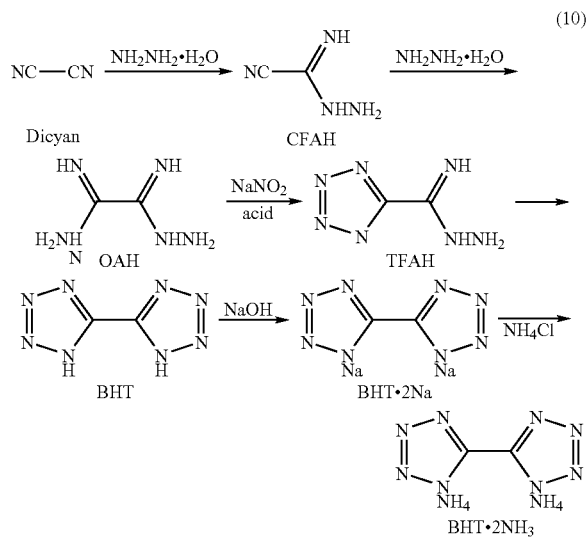

In the step of synthesizing the oxaldiimidic acid dihydrazide (OAH) according to the invention, the dicyan reacts with a molecule of hydrazine hydrate to form a 1-cyanoformimidic acid hydrazide (CFAH) and further reacts with another molecule of hydrazine hydrate to form the oxaldiimidic acid dihydrazide (OAH) as expressed by the above formula (10). When the hydrazine hydrate and the dicyan exist at a stoichiometric ratio (2:1), the reaction is not completed despite the reaction time is extended, and there remains an unstable 1-cyanoformimidic acid hydrazide (CFAH) which is an intermediate product, etc., causing a decrease in the purity of the isolated oxaldiimidic acid dihydrazide (OAH) and a decrease in the yield.

When the reaction is conducted at a temperature of not lower than 50° C., too, the intermediate reaction product and the oxaldiimidic acid dihydrazide (OAH) undergo the decomposition.

In order to obtain the oxaldiimidic acid dihydrazide (OAH) maintaining a high purity and a high yield, therefore, it is very important that the hydrazine hydrate is fed at a molar ratio of not smaller than at least the stoichiometric ratio and, particularly preferably, at a ratio of hydrazine hydrate/dicyan of from 2.5 to 3.5 (molar ratio), and that the reaction temperature is controlled to be from −10 to 50° C. and, particularly preferably, from 10 to 30° C.

In the step of synthesizing the 5,5'-bi-1H-tetrazolediammonium salt (BHT.2NH$_3$) of the present invention as represented by the above formula (10), the oxaldiimidic acid dihydrazide (OAH) is dissolved in a weakly acidic aqueous solution of pH of 4 to 6 and, then, an aqueous solution of sodium nitrite is added thereto to form an azide thereof and to effect the cyclization reaction by heating, thereby to form a 1H-tetrazoleformimidic acid hydrazide (TFAH). The reaction is further continued to form an azide thereof and to effect the cyclization reaction, in order to convert the 1H-tetrazoleformimidic acid hydrazide (TFAH) into the 5,5'-bi-1H-tetrazole (BHT). Next, an aqueous solution of sodium hydroxide is added to the 5,5'-bi-1H-tetrazole (BHT) reaction solution to convert it into the 5,5'-bi-1H-tetrazoledisodium salt (BHT.2Na). Then, about one-half amount of the reaction solution is condensed and is reacted with ammonium chloride or with an aqueous solution of ammonium chloride, whereby the formed 5,5'-bi-1H-tetrazolediammonium salt (BHT.2NH$_3$) is precipitated as crystals and is thus obtained in an yield of about 80% through a very simple operation of filtration and separation.

Under a strongly acidic condition, the oxaldiimidic acid dihydrazide (OAH) is decomposed predominantly, and the desired 5,5'-bi-1H-tetrazolediammonium salt (BHT.2NH$_3$) is obtained in a very low yield.

1) In the step of preparing the oxaldiimidic acid dihydrazide (OAH), the dicyan used for the reaction may be the one synthesized by a method that has been known per se. For example, a liquid dicyan synthesized from hydrogen cyanide/hydrogen peroxide water and copper sulfate/ferric chloride as a catalyst, or a gaseous dicyan generated by the preparation methods disclosed in Japanese Unexamined Patent Publications Nos. 7565/1971 and 38900/1972, is directly introduced into an aqueous solution of hydrazine hydrate in order to synthesize an oxaldiimidic acid dihydrazide (OAH) which is an intermediate product.

The dicyan may be added in either a gaseous form or as a liquid to the aqueous solution of hydrazine hydrate or to an alcohol/water mixed solution containing hydrazine hydrate. It is desired that the temperature at the time of addition is not higher than 30° C. The feeding molar ratio (hydrazine hydrate/dicyan) is not smaller than 2 but is not larger than 5 and, particularly preferably, from 2.5 to 3.5. When the molar ratio of hydrazine hydrate/dicyan=2 (stoichiometric amount), the reaction rate is very low and an unstable 1-cyanoformimidic acid hydrazide (CFAH) intermediate product remains. When the sparingly soluble oxaldiimidic acid dihydrazide (OAH) is isolated as crystals, therefore, the intermediate product infiltrates therein making it difficult to obtain an oxaldiimidic acid dihydrazide (OAH) maintaining a high purity and a high yield.

The reaction solvent may be an alcohol solvent such as methanol, ethanol, n-propanol or iso-propanol, water, or a water/alcohol mixed solvent.

After the dicyan has been added, the reaction is conducted for 2 to 30 hours at a temperature of from −10 to 50° C. and, particularly preferably, for 3 to 7 hours and at 10 to 30° C. in order to suppress the decomposition of the oxaldiimidic acid dihydrazide (OAH).

The progress of reaction can be traced by the liquid chromatography. That is, there can be observed a state in which the 1-cyanoformimidic acid hydrazide (CFAH) intermediate product reacts with another molecule of hydrazine hydrate and is converted into the oxaldiimidic acid dihydrazide (OAH), and whereby the 1-cyanoformimidic acid hydrazide (CFAH) decreases and the oxaldiimidic acid dihydrazide (OAH) increases. The reaction continues until the 1-cyanoformimidic acid hydrazide (CFAH) decreases to not larger than 1% (area percentage of liquid chromatography).

After the reaction has been finished, the reaction solution is cooled down to about 10° C., and the oxaldiimidic acid dihydrazide (OAH) is obtained maintaining a high yield of not lower than 95% and a high purity of not lower than 99% through a very simple operation of filtering and separating the precipitated crystals. The concentration of the oxaldiimidic acid dihydrazide (OAH) remaining in the isolated mother liquor is not higher than 0.2%. Besides, there is no contradiction in the balance of the hydrazine hydrate before and after the reaction.

2) In the step of preparing the 5,5'-bi-1H-tetrazolediammonium salt (BHY.2NH$_3$), the isolated oxaldimidic acid dihydrazide (OAH) is suspended in water, and a weakly acidic compound is added in a predetermined amount at a temperature of not higher than 10° C. to adjust the pH of the reaction solution to be from 4 to 6. The aqueous solution is cooled down to about 0° C. and, then, an aqueous solution of sodium nitrite is dropwisely added thereto to form the 1H-tetrazoleformimidic acid hydrazide (TFAH) through the reaction of forming an azide thereof and through the cyclization reaction by heating. By further continuing the reaction, white crystals of the 5,5'-bi-1H-tetrazole (BHT) are precipitated in the reaction solution. Then, an aqueous solution of sodium hydroxide is added to the reaction solution containing the 5,5'-bi-1H-tetrazole (BHT) to convert the 5,5'-bi-1H-tetrazole (BHT) into the 5,5'-bi-1H-tetrazoledisodium salt (BHT.2Na). Then, one-half of the reaction solution of the 5,5'-bi-1H-tetrazoledisodium salt (BHT.2Na) is condensed, and an aqueous solution of ammonium chloride is dropwisely added thereto under a heated condition to isolate the 5,5'-bi-1H-tetrazolediammonium salt (BHT.2NH$_3$) as sparingly soluble crystals.

The weakly acidic compound to be added to the aqueous suspension of the oxaldiimidic acid dihydrazide (OAH) will be acetic acid, formic acid, propionic acid, octanoic acid or citric acid having pKa=3 to 5. Among them, however, acetic acid is particularly desired. Upon adding the weakly acidic compound such as acetic acid or the like acid to the aqueous suspension of the oxaldiimidic acid dihydrazide (OAH), the reaction for forming an azide proceeds smoothly, and the 5,5'-bi-1H-tetrazolediammnium salt (BHT.2NH$_3$) is obtained maintaining an yield of as high as 80%.

Under a strongly acidic condition of using hydrochloric acid, nitric acid or the like acid, however, the oxaldimidic acid dihydrazide (OAH) decomposes predominantly, and the 5,5'-bi-1H-tetrazolediammonium salt (BHT.2NH$_3$) is obtained maintaining an yield of as very low as about 20%.

The feeding molar ratio of weakly acidic compound (B) such as acetic acid, sodium nitrite (C), sodium hydroxide (D) and ammonium chloride (E) per the oxaldimidic acid dihydrazide (OAH) is (A):(B):(C):(D):(E)=1:2 to 4:2 to 4:2 to 3.5:2 to 3.5. More particularly, (A):(B):(C):(D):(E)=1:2 to 2.5:2 to 2.4:2 to 3:2 to 3.

Water can be used as the reaction solvent. The hydrazine hydrate in the step of preparing the oxaldiimidic acid dihydrazide (OAH), and the weakly acidic compound, sodium nitrite, sodium hydroxide and ammonium chloride in the step of preparing the 5,5'-bi-1H-tetrazolediammonium salt (BHT.2NH$_3$) may be those that are produced on an industrial scale.

The weakly acidic compound such as acetic acid is added at a temperature of not higher than room temperature at which the decomposition of the oxaldiimidic acid dihydrazide (OAH) can be suppressed and, particularly preferably, at a temperature of not higher than 10° C. After the weakly acidic compound has been added, the oxaldiimidic acid dihydrazide (OAH) dissolves therein to form a homogeneous aqueous solution. The aqueous solution has a pH of from 4 to 6.

Next, after the weakly acidic compound has been added, the aqueous solution of sodium nitrite is dropwisely added to the aqueous solution at a temperature of not higher than 30° C. and, particularly preferably, not higher than 10° C. over a period of from 30 to 60 minutes. Thereafter, the temperature is elevated to room temperature over a period of about one hour, and the reaction is conducted at 40 to 50° C. for 1 to 5 hours to form the 1H-tetrazoleformimidic acid hydrazide (TFAH) which is an intermediate product through the formation of azide thereof and the cyclization reaction. The reaction is further continued to convert the intermediate product into the 5,5'-bi-1H-tetrazole (BHT).

The progress of the reaction, i.e., the conversion of the oxaldiimidic acid dihydrazide (OAH) into the 5,5'-bi-1H-tetrazole (BHT) through the 1H-tetrazoleformimidic acid hydrazide (TFAH), can be traced by the liquid chromatography. A moment at which the 1H-tetrazoleformimidic acid hydrazide (TFAH) decreases to not larger than 1% (area percentage of the liquid chromatograph) is regarded to be the end of the reaction.

Next, the aqueous solution of sodium hydroxide is added at 20 to 80° C. to conduct the reaction for 1 to 2 hours, whereby the 5,5'-bi-1H-tetrazole (BHT) is converted into the 5,5'-bi-1H-tetrazoledisodium salt (BHT.2Na), and about one-half amount of the reaction solution is condensed.

Further, the aqueous solution of ammonium chloride is dropwisely added at a temperature of from 40 to 80° C. over a period of about 30 minutes. Due to the reaction of the 5,5'-bi-1H-tetrazoledisodium salt (BHT.2Na) with the ammonium chloride, there is precipitated the desired 5,5'-bi-1H-tetrazolediammonium salt (BHT.2NH$_3$) as sparingly soluble white crystals.

After the reaction, the reaction solution is cooled down to 0 to 5° C., and the crystals are isolated, washed with water and dried to obtain the 5,5'-bi-1H-tetrazolediammonium salt (BHT.2NH$_3$) maintaining an yield of 80%.

According to the present invention, there is prepared the 5,5'-bi-1H-tetrazolediammonium salt (BHT.2NH$_3$) maintaining an yield of as high as 80% by quantitatively synthesizing and isolating the oxaldiimidic acid dihydrazide (OAH) from the starting materials of hydrazine hydrate and dicyan, subjecting the oxaldiimidic acid dihydrazide (OAH) to the formation of an azide thereof in a weakly acidic aqueous solution and to the cyclization reaction by heating, and filtering and separating the sparingly soluble 5,5'-bi-1H-tetrazolediammonium salt (BHT.2NH$_3$), which is a very simple operation.

Namely, it is necessary to isolate the oxaldiimidic acid dihydrazide (OAH) which is an intermediate product. In the step of forming the tetrazole by using the oxaldiimidic acid dihydrazide (OAH) as a starting material, however, a route of synthesizing the desired 5,5'-bi-1H-tetrazolediammonium salt (BHT.2NH$_3$) is established through a common (single) reaction system without at all isolating the intermediate product.

EXAMPLES

The invention will now be concretely described by way of Examples to which only, however, the invention is in no way limited.

The 5,5'-bi-1H-tetrazole (BHT), 1H-tetrazoleformimidic acid hydrazide (TFAH) intermediate product, 1-cyanoformimidic acid hydrazide (CFAH), oxaldiimidic acid dihydrazide (OAH) and hydrogen azide were analyzed by the liquid chromatography (HPLC), and the hydrogen cyanide and dicyan were analyzed by the gas chromatography (GC). The content of the 5,5'-bi-1H-tetrazolediammonium salt (BHT.2NH$_3$) was found by the titration with HClO$_4$ and by the liquid chromatography.

Reference Example 1

Synthesis of Dicyan [NC—CN]

12.56 Grams (0.050 mols) of 99.5% CuSO$_4$.H$_2$O, 12.76 g (0.025 mols) of 78.6% Fe$_2$(SO$_4$)$_3$, and 100.2 g of water were fed into a 500-ml flask and were stirred and dissolved. 49.9% HCN aqueous solution (feeding rate, 52.2 to 78.1 g/hr; feeding time, 3.5 hours; total weight of feed, 217.9 g (4.000 mols)) and 34.6% H$_2$O$_2$ aqueous solution (feeding rate, 39.6 to 86.6 g/hr; feeding time, 4 hours; total weight of feed, 236.8 g (2.409 mols)) were separately fed by using feed pumps into a CuSO$_4$—Fe$_2$(SO$_4$)$_3$ aqueous solution at a feeding temperature of from 6.8 to 14.6° C.

An NaOH aqueous solution was used as a trap, and the dicyan was synthesized in a closed reaction system. After the feed has been finished, the temperature was elevated up to 40° C. over one hour while effecting the bubbling with nitrogen in order to expel the dicyan out of the reaction solution. The formed dicyan was obtained in a glass container in a coolant cooled at −72 to −79° C.

The amount of the dicyan after the bubbling with nitrogen was 87.37 g, the weight yield was 84.0%, the weight of the reaction solution was 454.22 g [weight loss was 27.32 g], weight of NaOH trapped has increased by 11.07 g [CN component (AgNO$_3$ tit.), 0.0085 mols].

87.37 Grams of the obtained dicyan was vaporized at −15 to −20° C., liquefied and is filled in a pressure-resistant glass container in a coolant cooled at −50° C. The amount of the dicyan obtained was 80.42 g, the amount of the solution remaining after the vaporization was 3.47 g, and loss due to purification by vaporization was 3.48 g.

Next, the dicyan and hydrogen cyanide in the pressure-resistant glass container and in the solution remaining after the vaporization were analyzed by the gas chromatography. As a result, the amount of the hydrogen cyanide in the pressure-resistant glass container was smaller than a detectable limit, and the dicyan of a high purity (content: 99.99% (GC)) was obtained.

The yield of dicyan in the container: 77.3%

Feeding molar ratio of HCN:H$_2$O$_2$:CuSO$_4$:Fe$_2$(SO$_4$)$_3$=1: 0.6:0.0125:0.0063

Example 1

Synthesis of Oxaldiimidic Acid Dihydrazide (OAH)

25.04 Grams (0.500 mols) of 100% hydrazine hydrate, 56.40 g of MeOH and 18.79 g of H$_2$O were fed into a 200-ml four neck distillation flask [total feeding amount of 100.23 g]. After cooled, 12.57 g (0.242 mols) of dicyan was blown thereto at a blowing temperature of from −4.0 to 3.5° C. over a blowing time of 2 hours and 15 minutes.

112.80 Grams of the reaction solution to which the dicyan has been introduced was reacted with stirring at a temperature of from 3.5 to 25.2° C. for one hour and, then, with stirring at a temperature of from 25.2 to 19.9° C. (room temperature) for 3 hours. The progress of reaction was traced by the HPLC analysis. After stirred at room temperature for 3 hours, there were formed 28.12% of an oxaldiimidic acid dihydrazide (OAH) and 71.57% of 1-cyanoformimidic acid hydrazide (CFAH). Next, the reaction was conducted with stirring at a temperature of 19.9 to 7.5° C. for 19 hours.

However, OAH was 86.68%, CFAH was 13.32%, there remained an intermediate product, and the reaction was not conducted to a sufficient degree.

Therefore, 12.55 g (0.251 mols) of 100% hydrazine hydrate, 28.20 g of MeOH and 9.55 g of H$_2$O [total feeding amount of 50.30 g] were added at a temperature of from 13.6 to 17.8° C. over a period of 20 minutes. The progress of reaction was confirmed after every hour by the HPLC analysis, and the reaction was conducted with stirring at a temperature of from 18.3 to 17.9° C. for 3 hours.

After the addition, the stirring was effected for 1 hour to yield 97.02% of OAH and 2.98% of CFAH (HPLC area %).

After the addition, the stirring was effected for 2 hours to yield 98.42% of OAH and 1.58% of CFAH.

After the addition, the stirring was effected for 3 hours to yield 99.18% of OAH and 0.82% of CFAH.

After the reaction, 161.79 g of the reaction solution was cooled down to 3° C., and the precipitated crystals were separated and washed with 50 g of MeOH to isolate 38.06 g of wet crystals thereof. After drying in a vacuum drier at room temperature for 8 hours, there was obtained 27.63 g of white powdery crystals (OAH). The amount of the separation mother liquor+MeOH washing solution was 166.00 g.

[Yield and analytical values of the oxaldiimidic acid dihydrazide (OAH)]

Coarse crystals OAH content: HPLC 99.44% (area %), HCltit. 97.59% Obtained amount: 27.59 g (0.232 mols), hydrazine component (0.464 mols) Yield: 96.12% (on the basis of NC—CN), hydrazine recovery rate 61.84%

Mother liquor+MeOH washing solution OAH content: 0.19%, 0.32 g (0.003 mols), hydrazine component (0.269 mols), hydrazine recovery rate 35.83% Total yield: 97.24%, total hydrazine recovery rate 97.67%

Example 2

Synthesis of Oxaldiimidic Acid Dihydrazide (OAH)

75.11 Grams (1.500 mols) of 100% hydrazine hydrate, 169.11 g of MeOH and 56.34 g of H$_2$O were fed into a 500-ml four neck distillation flask [total feeding amount of 300.65 g]. After cooled, 26.09 g (0.501 mols) of dicyan was blown thereto at a blowing temperature of from −0.4 to 3.5° C. over a blowing time of 2 hours and 25 minutes.

326.74 Grams of the reaction solution to which the dicyan has been introduced was reacted with stirring at a temperature of from 3.5 to 26.5° C. for one hour and, then, with stirring at a temperature of from 26.5 to 21.6° C. (room temperature) for 4 hours. The progress of reaction was traced after every hour by the HPLC analysis.

After the addition, no stirring was effected to yield 41.06% of OAH and 58.53% of CFAH (HPLC area %).

After the addition, the stirring was effected for 1 hour to yield 69.46% of OAH and 29.63% of CFAH.

After the addition, the stirring was effected for 2 hours to yield 87.84% of OAH and 11.22% of CFAH.

After the addition, the stirring was effected for 3 hours to yield 94.53% of OAH and 4.85% of CFAH.

After the addition, the stirring was effected for 4 hours to yield 97.43% of OAH and 1.98% of CFAH.

After the addition, the stirring was effected for 5 hours to yield 98.64% of OAH and 0.82% of CFAH.

After the reaction, 326.30 g of the reaction solution was cooled down to 4.1° C., and the precipitated crystals were separated and washed with 51.5 g of MeOH to isolate 73.00 g of wet crystals thereof. After drying in a vacuum drier at room temperature for 8 hours, there was obtained 58.16 g of white powdery crystals (OAH). The amount of the separation mother liquor+MeOH washing solution was 295.96 g.

[Yield and analytical values of the oxaldiimidic acid dihydrazide (OAH)]

Coarse crystals OAH content: HPLC 99.55% (area %), HCltit. 98.76% Obtained amount: 58.16 g (0.495 mols), hydrazine component (0.989 mols) Yield: 98.65% (on the basis of NC—CN), hydrazine recovery rate 65.93%

Mother liquor+MeOH washing solution OAH content: 0.22%, 0.65 g (0.006 mols), hydrazine component (0.504 mols), hydrazine recovery rate 33.61% Total yield: 99.76%, total hydrazine recovery rate 99.54%

Example 3

Synthesis of Oxaldiimidic Acid Dihydrazide (OAH)

75.11 Grams (1.500 mols) of 100% hydrazine hydrate, 169.32 g of MeOH and 56.42 g of $H_2O$ were fed into a 500-ml four neck distillation flask [total feeding amount of 300.85 g]. After cooled, 25.91 g (0.498 mols) of dicyan was blown thereto at a blowing temperature of from 24.9 to 27.7° C. over a blowing time of 2 hours and 45 minutes.

326.76 Grams of the reaction solution to which the dicyan has been introduced was reacted with stirring at a temperature of from 27.4 to 25.0° C. for one hour and, then, with stirring at a temperature of from 25.0 to 18.9° C. for 3 hours. The progress of reaction was traced after every hour by the HPLC analysis.

After the addition, no stirring was effected to yield 82.89% of OAH and 16.52% of CFAH (HPLC area %).

After the addition, the stirring was effected for 1 hour to yield 92.76% of OAH and 6.12% of CFAH.

After the addition, the stirring was effected for 2 hours to yield 95.68% of OAH and 3.64% of CFAH.

After the addition, the stirring was effected for 3 hours to yield 97.98% of OAH and 1.38 of CFAH.

After the addition, the stirring was effected for 4 hours to yield 99.09 of OAH and 0.28% of CFAH.

After the reaction, 326.59 g of the reaction solution was cooled down to 2.0° C., and the precipitated crystals were separated and washed with 49.7 g of MeOH to isolate 69.46 g of wet crystals thereof. After drying in a vacuum drier at room temperature for 8 hours, there was obtained 56.17 g of white powdery crystals (OAH). The amount of the separation mother liquor+MeOH washing solution was 297.22 g.

[Yield and analytical values of the oxaldiimidic acid dihydrazide (OAH)]

Coarse crystals OAH content: HPLC 99.48% (area %), HCltit. 99.70% Obtained amount: 56.17 g (0.482 mols), hydrazine component (0.965 mols) Yield: 96.85% (on the basis of NC—CN), hydrazine recovery rate 64.28%

Mother liquor+MeOH washing solution OAH content: 0.21%, 0.62 g (0.005 mols), hydrazine component (0.506 mols), hydrazine recovery rate 33.69% Total yield: 97.93%, total hydrazine recovery rate 97.97%

Comparative Example 1

Synthesis of Oxaldiimidic Acid Dihydrazide (OAH)[Trace Experiment of the Literature]

50.06 Grams (1.000 mol) of 100% hydrazine hydrate, 50.0 g of EtOH and 50.0 g of $H_2O$ were fed into a 300-ml four neck distillation flask [total feeding amount of 150.06 g]. After cooled, 26.02 g (0.500 mols) of dicyan was blown thereto at a blowing temperature of from −4.0 to 4.2 ° C. over a blowing time of 1 hour and 30 minutes.

The reaction solution to which the dicyan has been introduced was reacted with stirring at a temperature of from −3.7 to 4.2° C. for 2 hours. The precipitated crystals were separated and washed with 28.0 g of 20% EtOH to isolate 41.2 g of wet crystals thereof. After drying in a vacuum drier at room temperature for 5 hours, there was obtained 27.0 g of brownish white powdery crystals (OAH). The amount of the separation mother liquor+EtOH washing solution was 126.4 g.

[Yield and analytical values of the oxaldiimidic acid dihydrazide (OAH)]

Coarse crystals OAH content: HPLC 98.47% (area %), HCltit. 95.58% Yield: 44.4% (on the basis of hydrazine hydrate)

Example 4

Synthesis of 5,5'-bi-1H-tetrazolediammonium Salt [BHT.2NH$_3$]

11.76 Grams (0.100 mol) of 98.76% oxaldiimidic acid dihydrazide (Example 2)(OAH) and 100.13 g of $H_2O$ were fed into a 500-ml distillation flask, and were cooled down to 5° C. in a slurry state. A mixed aqueous solution of 13.34 g (0.220 mols) of 99.0% acetic acid and 13.52 g of $H_2O$ was added thereto dropwise at a temperature of 3.8 to 5.6° C. over a period of 5 minutes. The OAH crystals have dissolved accompanying the dropwise addition of acetic acid, and the solution has changed into a faintly yellow transparent solution. The pH of the reaction solution was 4.

Next, 15.45 g (0.220 mols) of 98.5% $NaNO_2$ and 31.94 g of $H_2O$ were added dropwise thereto at a temperature of from −6.1 to 4.4° C. over a period of 35 minutes. After the dropwise addition has been completed, the reaction was conducted at a temperature of from −5.3 to 17.0° C. for 3 hours and 30 minutes. To improve the stirring condition, 31.94 g of $H_2O$ was added thereto.

Thereafter, 29.14 g (0.220 mols) of 30.24% NaOH aqueous solution was added thereto dropwise at a temperature of from 16.7 to 20.1° C. over a period of 15 minutes to convert the 5,5'-bi-1H-tetrazole into a 5,5'-bi-1H-tetrazoledisodium salt.

A brown reaction solution was heated at 65° C., and 11.89 g (0.220 mols) of 99.0% $NH_4CL$ and 31.70 g of $H_2O$ were added thereto dropwise at a temperature of 64.5 to 64.6° C.

over a period of 15 minutes to synthesize a 5,5'-bi-1H-tetrazolediammonium salt [BHT.2NH₃] by the reaction of the 5,5'-bi-1H-tetrazoledisodium salt [BHT.2Na] with the NH₄CL.

After the NH₄CL aqueous solution has been dropwisely added thereto, 307.02 g of the reaction solution was cooled down to 6.5° C., and the precipitated crystals were separated and washed with 50.5 g of H₂O to isolate 18.58 g of the wet 5,5'-bi-1H-tetrazolediammonium salt [BHT.2NH₃]. After drying in a vacuum drier at a drying temperature of 50° C. for 6 hours, there was obtained 10.61 g of the 5,5'-bi-1H-tetrazolediammonium salt [BHT.2NH₃](yellow powder). The total amount of the separation mother liquor+washing solution was 335.24 g.

The feeding mol ratio of OAH:AcOH:NaNO₂:NaOH:NH₄Cl was 1.0:2.2:2.2:2.2:2.2.

[Yield and analytical values of 5,5'-bi-1H-tetrazolediammonium salt [BHT.2NH₃]]Yield of coarse crystals: 61.6% on the basis of OAH Analytical values of coarse crystals: HClO₄tit. 99.85%, HPLC 96.58% (area %)

(Separation mother liquor+washing solution) analytical value: [BHT.2NH₃], 0.74% by weight, 2.48 g (0.014 mols) Total [BHT.2NH₃] yield (coarse crystals+mother liquor+washing solution): 76.0% on the basis of OAH Example 5

Synthesis of 5,5'-bi-1H-tetrazolediammonium Salt [BHT.2NH₃]

11.76 Grams (0.100 mol) of 98.76% oxaldiimidic acid dihydrazide (Example 2)(OAH) and 150.1 g of H₂O were fed into a 500-ml distillation flask, and were cooled down to 0° C. in a slurry state. A mixed aqueous solution of 12.13 g (0.200 mols) of 99.0% acetic acid and 12.05 g of H₂O was added thereto dropwise at a temperature of −4.7 to 3.3° C. over a period of one hour. The OAH crystals have dissolved accompanying the dropwise addition of acetic acid, and the solution has changed into a faintly yellow transparent solution. The pH of the reaction solution was 4.

Next, 15.41 g (0.220 mols) of 98.5% NaNO₂ and 30.07 g of H₂O were added dropwise thereto at a temperature of from −4.4 to 1.0° C. over a period of one hour. After the dropwise addition has been completed, the reaction was conducted at a temperature of from −4.8 to 22.7° C. for one hour and, then, at 23.7 to 24.0° C. for 5 hours.

Thereafter, 27.92 g (0.211 mols) of 30.24% NaOH aqueous solution was added thereto dropwise at a temperature of from 70.3 to 70.8° C. over a period of 25 minutes.

After the NaOH aqueous solution has been dropwisely added thereto, the faint yellowish reaction solution was heated at 70° C. to conduct the reaction at a temperature of from 68.4 to 70.8° C. for 2 hours in order to convert the 5,5'-bi-1H-tetrazole into a 5,5'-bi-1H-tetrazoledisodium salt.

12.43 Grams (0.230 mols) of 99.0% NH₄CL and 33.59 g of H₂O were added at a temperature of 70.3 to 70.5° C. over a period of 20 minutes to synthesize a 5,5'-bi-1H-tetrazolediammonium salt [BHT.2NH₃] by the reaction of the 5,5'-bi-1H-tetrazoledisodium salt [BHT.2Na] with the NH₄CL.

After the NH₄CL aqueous solution has been dropwisely added thereto, 301.02 g of the reaction solution was cooled down to 10.3° C., and the precipitated crystals were separated and washed with 50.4 g of H₂O to isolate 19.80 g of the wet 5,5'-bi-1H-tetrazolediammonium salt [BHT.2NH₃]. After drying in a vacuum drier at a drying temperature of 50° C. for 6 hours, there was obtained 10.65 g of the 5,5'-bi-1H-tetrazolediammonium salt [BHT.2NH₃](yellow powder). The total amount of the separation mother liquor+washing solution was 327.91 g.

The feeding mol ratio of OAH:AcOH:NaNO₂:NaOH:NH₄Cl was 1.0:2.0:2.2:2.1:2.3.

[Yield and analytical values of 5,5'-bi-1H-tetrazolediammonium salt [BHT.2NH₃]]Yield of coarse crystals: 58.7% on the basis of OAH Analytical values of coarse crystals: HClO₄tit. 95.15%, HPLC 98.09% (area %)

(Separation mother liquor+washing solution) analytical value: [BHT.2NH₃], 0.70% by weight, 2.30 g (0.013 mols) Total [BHT.2NH₃] yield (coarse crystals+mother liquor+washing solution): 72.2% on the basis of OAH Example 6

Synthesis of 5,5'-bi-1H-tetrazolediammonium Salt [BHT.2NH₃]

11.65 Grams (0.100 mol) of 99.7% oxaldiimidic acid dihydrazide (Example 3)(OAH) and 100.03 g of H₂O were fed into a 300-ml distillation flask, and was cooled down to 0° C. in a slurry state. 16.81 Grams (0.240 mols) of 98.5% NaNO₂ and 30.00 g of H₂O were added thereto dropwise at a temperature of −0.1 to 0.5° C. over a period of 25 minutes. After the NaNO₂ aqueous solution has been dropwisely added, the reaction was conducted at a temperature of from −0.1 to 25.6° C. for one hour, at 23.4 to 25.0° C. for 2 hours and at 48.2 to 51.1° C. for 4 hours.

Next, the reaction solution was cooled, and a mixed aqueous solution of 14.46 g (0.240 mols) of 99.0% acetic acid and 14.50 g of H₂O was added thereto dropwise at a temperature of from 9.4 to 54.2° C. over a period of 35 minutes. Accompanying the dropwise addition of acetic acid, the pH of the reaction solution has changed from pH=8 (of before acetic acid was added) to pH=4 (yellow slurry solution) accompanied by foaming, vigorous generation of heat, dissolution of crystals and precipitation of crystals. After the dropwise addition has been finished, the reaction was conducted at a temperature of from 25.4 to 25.6° C. for 2 hours and at 50.2 to 50.9° C. for one hour.

Thereafter, the reaction solution was cooled, and 27.78 g (0.210 mols) of 30.24% NaOH aqueous solution was added dropwise at a temperature of from 31.0 to 35.3° C. over a period of 7 minutes. After the dropwise addition of NaOH aqueous solution has been finished, the faintly yellow reaction solution was heated at 80° C. to conduct the reaction at 79.0 to 81.2° C. for 2 hours in order to convert the 5,5'-bi-1H-tetrazole into a 5,5'-bi-1H-tetrazoledisodium salt.

12.43 Grams g (0.230 mols) of 99.0% NH₄CL and 33.40 g of H₂O were added thereto dropwise at a temperature of 78.7 to 80.3° C. over a period of 10 minutes to synthesize a 5,5'-bi-1H-tetrazolediammonium salt [BHT.2NH₃] by the reaction of the 5,5'-bi-1H-tetrazoledisodium salt [BHT.2Na] with the NH₄CL.

After the NH₄CL aqueous solution has been dropwisely added thereto, 256.48 g of the reaction solution was cooled down to 0.7° C., and the precipitated crystals were separated and washed with 50.0 g of H₂O to isolate 23.01 g of the wet 5,5'-bi-1H-tetrazolediammonium salt [BHT.2NH₃]. After drying in a vacuum drier at a drying temperature of 50° C. for 6 hours, there was obtained 10.54 g of the 5,5'-bi-1H-tetrazolediammonium salt [BHT.2NH₃](nearly white powder). The total amount of the separation mother liquor+washing solution was 278.70 g.

The feeding mol ratio of OAH:AcOH:NaNO₂:NaOH:NH₄Cl was 1.0:2.4:2.4:2.1:2.3.

[Yield and analytical values of 5,5'-bi-1H-tetrazolediammonium salt [BHT.2NH₃]]Yield of coarse crystals: 58.6% on the basis of OAH Analytical values of coarse crystals: HClO₄tit. 95.64%, HPLC 95.61% (area %)

(Separation mother liquor+washing solution) analytical value: [BHT.2NH₃], 0.87% by weight, 2.42 g (0.014 mols) Total [BHT.2NH₃] yield (coarse crystals+mother liquor+washing solution): 72.6% on the basis of OAH Example 7

Synthesis of 5,5'-bi-1H-tetrazolediammonium Salt [BHT.2NH₃]

5.82 Grams (0.050 mol) of 99.70% oxaldiimidic acid dihydrazide (Example 3)(OAH) and 50.0 g of H₂O were fed into a 200-ml distillation flask, and were cooled down to 10° C. in a slurry state. A mixed aqueous solution of 7.81 g (0.060 mols) of propionic anhydride and 8.90 g of H₂O was added thereto dropwise at a temperature of 11° C. over a period of 2 minutes. Next, 8.41 g (0.120 mol) of 98.5% NaNO₂ and 15.0 g of H₂O were added thereto dropwise at a temperature of from −3.8 to 2.5° C. over a period of 10 minutes. After the dropwise addition has been finished, the reaction was conducted at a temperature of from 3.8 to 16.8° C. for one hour, at 25.1 to 29.1° C. for 3 hours and 30 minutes and at 49.8 to 50.1° C. for 5 hours.

Next, the reaction solution was cooled, and 15.87 g (0.120 mols) of 30.24% NaOH aqueous solution was added thereto dropwise at a temperature of from 39.7 to 40.3° C. over a period of 13 minutes. After the dropwise addition of the NaOH aqueous solution has been finished, the brown reaction solution was heated at 80° C., and the reaction was conducted at a temperature of from 79.2 to 80.9° C. for 2 hours to convert the 5,5'-bi-1H-tetrazole into a 5,5'-bi-1H-tetrazoledisodium salt.

7.13 Grams g (0.132 mols) of 99.0% NH₄CL and 19.26 g of H₂O were added thereto dropwise at a temperature of 71.6 to 72.5° C. over a period of 10 minutes to synthesize a 5,5'-bi-1H-tetrazolediammonium salt [BHT.2NH₃] by the reaction of the 5,5'-bi-1H-tetrazoledisodium salt [BHT.2Na] with the NH₄CL.

After the NH₄CL aqueous solution has been dropwisely added thereto, the reaction solution was cooled, and the precipitated crystals were separated and washed with 20.1 g of H₂O to isolate 12.59 g of the wet 5,5'-bi-1H-tetrazolediammonium salt [BHT.2NH₃]. After drying in a vacuum drier at a drying temperature of 50° C. for 6 hours, there was obtained 4.18 g of the 5,5'-bi-1H-tetrazolediammonium salt [BHT.2NH₃]. The total amount of the separation mother liquor+washing solution was 198.78 g.

The feeding mol ratio of OAH:propionic anhydride:NaNO₂:NaOH:NH₄Cl was 1.0:2.4:2.4:2.4:2.65.

[Yield and analytical values of 5,5'-bi-1H-tetrazolediammonium salt [BHT.2NH₃]]Yield of coarse crystals: 47.0% on the basis of OAH Analytical values of coarse crystals: HClO₄tit. 95.15%, (Separation mother liquor+washing solution) analytical value: [BHT.2NH₃], 1.00% by weight, 1.98 g (0.012 mols) Total [BHT.2NH₃] yield (coarse crystals+mother liquor+washing solution): 69.9% on the basis of OAH Example 8

Synthesis of 5,5'-bi-1H-tetrazolediammonium Salt [BHT.2NH₃]

2.33 Grams (0.020 mol) of 99.70% oxaldiimidic acid dihydrazide (Example 3)(OAH) and 30.0 g of H₂O were fed into a 100-ml distillation flask, and to which was dropwisely added 6.99 g (0.048 mols) of 99% octanoic acid in a slurry state and in a heated condition at a temperature of 12.7 to 23.0° C. over a period of 15 minutes.

Next, 3.36 g (0.048 mols) of 98.5% NaNO₂ and 6.0 g of H₂O were added thereto dropwise at a temperature of 22.2 to 27.0° C. over a period of 10 minutes. After the dropwise addition has been finished, the reaction was conducted at a temperature of from 32.2 to 37.5° C. for 21 hours.

Thereafter, 6.35 g (0.048 mols) of 30.24% NaOH aqueous solution was dropwisely added thereto at a temperature of from 35.6 to 36.1° C. over a period of 3 minutes.

After the dropwise addition of NaOH aqueous solution has been finished, the brown reaction solution was heated at 80° C. to conduct the reaction at 77.7 to 79.9° C. for 2 hours in order to convert the 5,5'-bi-1H-tetrazole into a 5,5'-bi-1H-tetrazoledisodium salt.

2.85 Grams g (0.053 mols) of 99.0% NH₄CL and 7.70 g of H₂O were added thereto dropwise at a temperature of 76.4 to 76.7° C. over a period of 20 minutes to synthesize a 5,5'-bi-1H-tetrazolediammonium salt [BHT.2NH₃] by the reaction of the 5,5'-bi-1H-tetrazoledisodium salt [BHT.2Na] with the NH₄CL.

After the NH₄CL aqueous solution has been dropwisely added thereto, the reaction solution was cooled down to −0.1° C., and the precipitated crystals were separated and washed with 20.0 g of H₂O to isolate 6.14 g of the wet 5,5'-bi-1H-tetrazolediammonium salt [BHT.2NH₃]. After drying in a vacuum drier at a drying temperature of 50° C. for 6 hours, there was obtained 2.37 g of the 5,5'-bi-1H-tetrazolediammonium salt [BHT.2NH₃]. The total amount of the separation mother liquor+washing solution was 77.21 g.

The feeding mol ratio of OAH:octanoic acid:NaNO₂:NaOH:NH₄Cl was 1.0:2.4:2.4:2.4:2.65.

[Yield and analytical values of 5,5'-bi-1H-tetrazolediammonium salt [BHT.2NH₃]]Yield of coarse crystals: 51.9% on the basis of OAH Analytical values of coarse crystals: HClO₄tit. 75.36%, HPLC 88.97% (area %)

(Separation mother liquor+washing solution) analytical value: [BHT.2NH₃], 0.61% by weight, 0.47 g (0.003 mols) Total [BHT.2NH₃] yield (coarse crystals+mother liquor+washing solution): 65.5% on the basis of OAH Example 9

Synthesis of 5,5'-bi-1H-tetrazolediammonium Salt [BHT.2NH₃]

2.33 Grams (0.020 mol) of 99.70% oxaldiimidic acid dihydrazide (Example 3)(OAH) and 30.0 g of H₂O were fed into a 100-ml distillation flask, and were cooled down to 0° C. in a slurry state. A mixed aqueous solution of 2.45 g (0.048 mols) of 90% formic acid and 8.90 g of H₂O was added thereto dropwise at a temperature of from 0.2 to 4.3° C. over a period of 10 minutes.

Next, 3.36 g (0.048 mols) of 98.5% NaNO₂ and 6.0 g of H₂O were added thereto dropwise at a temperature of from −1.2 to 1.9° C. over a period of 45 minutes. After the dropwise addition has been finished, the reaction was conducted at a temperature of from −1.5 to 25.0° C. for one hour and at 25.0 to 28.9° C. for 2 hours.

Thereafter, 6.35 g (0.048 mols) of 30.24% NaOH aqueous solution was dropwisely added thereto at a temperature of from 24.5 to 28.9° C. over a period of 3 minutes.

After the dropwise addition of NaOH aqueous solution has been finished, the brown reaction solution was heated at 80° C. to conduct the reaction at 77.6 to 80.3° C. for 2 hours in order to convert the 5,5'-bi-1H-tetrazole into a 5,5'-bi-1H-tetrazolediisodium salt.

2.85 Grams g (0.053 mols) of 99.0% $NH_4CL$ and 7.70 g of $H_2O$ were added thereto dropwise at a temperature of 79.8 to 80.8° C. over a period of 20 minutes to synthesize a 5,5'-bi-1H-tetrazolediammonium salt [BHT.2NH$_3$] by the reaction of the 5,5'-bi-1H-tetrazolediisodium salt [BHT.2Na] with the $NH_4CL$.

After the $NH_4Cl$ aqueous solution has been dropwisely added thereto, the reaction solution was cooled down to −0.1° C., and the precipitated crystals were separated and washed with 20.0 g of $H_2O$ to isolate 5.10 g of the wet 5,5'-bi-1H-tetrazolediammonium salt [BHT.2NH$_3$]. After drying in a vacuum drier at a drying temperature of 50° C. for 6 hours, there was obtained 2.38 g of the 5,5'-bi-1H-tetrazolediammonium salt [BHT.2NH$_3$]. The total amount of the separation mother liquor+washing solution was 74.27 g.

The feeding mol ratio of OAH:formic acid:$NaNO_2$:NaOH:$NH_4Cl$ was 1.0:2.4:2.4:2.4:2.65.

[Yield and analytical values of 5,5'-bi-1H-tetrazolediammonium salt [BHT.2NH$_3$]]Yield of coarse crystals: 48.3% on the basis of OAH Analytical values of coarse crystals: $HClO_4$tit. 69.91%, HPLC 97.12% (area %)

(Separation mother liquor+washing solution) analytical value: [BHT.2NH$_3$], 0.40% by weight, 0.30 g (0.002 mols) Total [BHT.2NH$_3$] yield (coarse crystals+mother liquor+washing solution): 57.0% on the basis of OAH Example 10

Synthesis of 5,5'-bi-1H-tetrazolediammonium Salt [BHT.2NH$_3$]

5.82 Grams (0.050 mol) of 99.70% oxaldiimidic acid dihydrazide (Example 3)(OAH) and 50.0 g of $H_2O$ were fed into a 200-ml distillation flask, and were cooled down to 0° C. in a slurry state. A mixed aqueous solution of 7.84 g (0.040 mols) of 98% citric acid and 10.0 g of $H_2O$ was added thereto dropwise at a temperature of from −2.0 to −1.4° C. over a period of 20 minutes.

Next, 8.40 g (0.120 mols) of 98.5% $NaNO_2$ and 15.0 g of $H_2O$ were added thereto dropwise at a temperature of from 0.1 to 4.4° C. over a period of 30 minutes. After the dropwise addition has been finished, the reaction was conducted at a temperature of from 1.8 to 25.0° C. for one hour and at 25.5 to 27.1° C. for 4 hours and 30 minutes.

Thereafter, 15.87 g (0.120 mols) of 30.24% NaOH aqueous solution was dropwisely added thereto at a temperature of from 28.6 to 31.5° C. over a period of 5 minutes.

After the dropwise addition of NaOH aqueous solution has been finished, the brown reaction solution was heated at 80° C. to conduct the reaction at 77.1 to 80.7° C. for 2 hours in order to convert the 5,5'-bi-1H-tetrazole into a 5,5'-bi-1H-tetrazolediisodium salt.

7.13 Grams g (0.132 mols) of 99.0% $NH_4Cl$ and 19.3 g of $H_2O$ were added thereto dropwise at a temperature of 78.3 to 80.0° C. over a period of 20 minutes to synthesize a 5,5'-bi-1H-tetrazolediammonium salt [BHT.2NH$_3$] by the reaction of the 5,5'-bi-1H-tetrazolediisodium salt [BHT.2Na] with the $NH_4CL$.

After the $NH_4Cl$ aqueous solution has been dropwisely added thereto, the reaction solution was cooled down to 0.9° C., and the precipitated crystals were separated and washed with 50.0 g of $H_2O$ to isolate 11.48 g of the wet 5,5'-bi-1H-tetrazolediammonium salt [BHT.2NH$_3$]. After drying in a vacuum drier at a drying temperature of 50° C. for 6 hours, there was obtained 5.41 g of the 5,5'-bi-1H-tetrazolediammonium salt [BHT.2NH$_3$]. The total amount of the separation mother liquor+washing solution was 171.07 g.

The feeding mol ratio of OAH:citric acid:$NaNO_2$:NaOH:$NH_4Cl$ was 1.0:2.4:2.4:2.4:2.64.

[Yield and analytical values of 5,5'-bi-1H-tetrazolediammonium salt [BHT.2NH$_3$]]Yield of coarse crystals: 61.6% on the basis of OAH Analytical values of coarse crystals: $HClO_4$tit. 98.07%, HPLC 96.28% (area %)

(Separation mother liquor+washing solution) analytical value: [BHT.2NH$_3$], 0.54% by weight, 0.93 g (0.005 mols) Total [BHT.2NH$_3$] yield (coarse crystals+mother liquor+washing solution): 72.4% on the basis of OAH Example 11

Synthesis of 5,5'-bi-1H-tetrazolediammonium salt [BHT.2NH$_3$]

5.82 Grams (0.050 mol) of 98.76% oxaldiimidic acid dihydrazide (Example 2)(OAH) and 50.0 g of $H_2O$ were fed into a 200-ml distillation flask, and were cooled down to not higher than 0° C. in a slurry state. A mixed aqueous solution of 7.22 g (0.120 mols) of 99.7% acetic acid and 7.5 g of $H_2O$ was added thereto dropwise at a temperature of from −2.6 to 3.2° C. over a period of 10 minutes.

Next, 8.40 g (0.120 mols) of 98.5% $NaNO_2$ and 10.0 g of $H_2O$ were added thereto dropwise at a temperature of from −4.1 to 0.2° C. over a period of 40 minutes. After the dropwise addition has been finished, the reaction was conducted at a temperature of from −3.3 to 20.7° C. for one hour and at 24.2 to 24.6° C. for 2 hours.

Thereafter, 20.41 g (0.123 mols) of 30.24% NaOH aqueous solution was dropwisely added thereto at a temperature of from 25.8 to 31.2° C. over a period of 10 minutes.

After the dropwise addition of NaOH aqueous solution has been finished, the brown reaction solution was heated at 80° C. to conduct the reaction at 77.2 to 77.6° C. for 2 hours in order to convert the 5,5'-bi-1H-tetrazole into a 5,5'-bi-1H-tetrazolediisodium salt.

After the reaction, to 47.27 g of a condensed reaction solution obtained by condensing about one-half of 102.72 g of the reaction solution under a reduced pressure, there was dropwisely added 9.15 g (0.169 mols) of 99.0% $NH_4Cl$ and 24.78 g of $H_2O$ at a temperature of from 77.4 to 78.9° C. over a period of 30 minutes. A 5,5'-bi-1H-tetrazolediammonium salt [BHT.2NH$_3$] was synthesized by the reaction of the 5,5'-bi-1H-tetrazolediisodium salt [BHT.2Na] with the $NH_4CL$.

After the $NH_4Cl$ aqueous solution has been dropwisely added thereto, the reaction solution was cooled down to 1.4° C., and the precipitated crystals were separated and washed with 20.5 g of $H_2O$ to isolate 13.35 g of the wet 5,5'-bi-1H-tetrazolediammonium salt [BHT.2NH$_3$]. After drying in a vacuum drier at a drying temperature of 50° C. for 6 hours, there was obtained 6.87 g of the 5,5'-bi-1H-tetrazolediammonium salt [BHT.2NH$_3$](faint yellow). The total amount of the separation mother liquor+washing solution was 88.67 g.

The feeding mol ratio of OAH:AcOH:$NaNO_2$:NaOH:$NH_4Cl$ was 1.0:2.4:2.4:3.0:3.4.

[Yield and analytical values of 5,5'-bi-1H-tetrazolediammonium salt [BHT.2NH$_3$]]Yield of coarse crystals: 76.4% on the basis of OAH Analytical values of coarse crystals: $HClO_4$tit. 93.28%, HPLC 95.64% (area %)

(Separation mother liquor+washing solution) analytical value: [BHT.2NH$_3$], 0.40% by weight, 0.35 g (0.002 mols)

Total [BHT.2NH$_3$] yield (coarse crystals+mother liquor+washing solution): 80.4% on the basis of OAH

Example 12

Synthesis of 5,5'-bi-1H-tetrazolediammonium Salt [BHT.2NH$_3$]

11.71 Grams (0.100 mol) of 99.20% oxaldiimidic acid dihydrazide (OAH) and 100.0 g of H$_2$O were fed into a 300-ml distillation flask, and were cooled down to 0° C. in a slurry state. A mixed aqueous solution of 14.44 g (0.240 mols) of 99.7% acetic acid and 15.0 g of H$_2$O was added thereto dropwise at a temperature of from 0.4 to 3.0° C. over a period of 10 minutes.

Next, 16.81 g (0.240 mols) of 98.5% NaNO$_2$ and 30.0 g of H$_2$O were added thereto dropwise at a temperature of from −1.5 to 2.3° C. over a period of one hour and 10 minutes. After the dropwise addition has been finished, the reaction was conducted at a temperature of from −1.0 to 27.2° C. for one hour, at 24.2 to 25.7° C. for 2 hours and at 50.1 to 50.7° C. for 2 hours.

Thereafter, 31.75 g (0.240 mols) of 30.24% NaOH aqueous solution was dropwisely added thereto at a temperature of from 15.3 to 19.2° C. over a period of 10 minutes.

After the dropwise addition of NaOH aqueous solution has been finished, the brown reaction solution was heated at 80° C. to conduct the reaction at 80.0 to 82.7° C. for 2 hours in order to convert the 5,5'-bi-1H-tetrazole into a 5,5'-bi-1H-tetrazolediisodium salt.

After the reaction, to 102.82 g of a condensed reaction solution obtained by condensing about one-half of 217.87 g of the reaction solution under a reduced pressure, there was dropwisely added 14.26 g (0.264 mols) of 99.0% NH$_4$Cl and 38.60 g of H$_2$O at a temperature of from 79.0 to 81.6° C. over a period of 20 minutes. A 5,5'-bi-1H-tetrazolediammonium salt [BHT.2NH$_3$] was synthesized by the reaction of the 5,5'-bi-1H-tetrazoledisodium salt [BHT.2Na] with the NH$_4$CL.

After the NH$_4$Cl aqueous solution has been dropwisely added thereto, the reaction solution was cooled down to 0.8° C., and the precipitated crystals were separated and washed with 40.0 g of H$_2$O to isolate 40.07 g of the wet 5,5'-bi-1H-tetrazolediammonium salt [BHT.2NH$_3$]. After drying in a vacuum drier at a drying temperature of 50° C. for 6 hours, there was obtained 16.38 g of the 5,5'-bi-1H-tetrazolediammonium salt [BHT.2NH$_3$](faint yellow). The total amount of the separation mother liquor+washing solution was 155.89 g.

The feeding mol ratio of OAH:AcOH:NaNO$_2$:NaOH:NH$_4$Cl was 1.0:2.4:2.4:3.0:2.6.

[Yield and analytical values of 5,5'-bi-1H-tetrazolediammonium salt [BHT.2NH$_3$]]Yield of coarse crystals: 81.7% on the basis of OAH Analytical values of coarse crystals: HClO$_4$tit. 85.83%, HPLC 92.97% (area %)

(Separation mother liquor+washing solution) analytical value: [BHT.2NH$_3$], 0.60% by weight, 0.35 g (0.006 mols) Total [BHT.2NH$_3$] yield (coarse crystals+mother liquor+washing solution): 87.1% on the basis of OAH

Comparative Example 2

Synthesis of 5,5'-bi-1H-tetrazolediammonium Salt [BHT.2NH$_3$](trace experiment of the literature)

10.01 Grams (0.080 mol) of 93.04% oxaldiimidic acid dihydrazide (OAH) and 200.78 g of H$_2$O were fed into a 500-ml distillation flask, and were cooled down to 10° C. in a slurry state. A mixed aqueous solution of 26.6 g (0.252 mols) of 60% HNO$_3$ and 26.6 g of H$_2$O was added thereto dropwise at a temperature of from 9.2 to 11.2° C. over a period of 10 minutes.

Next, 25.7 g (0.151 mols) of 99.9% AgNO$_3$ was added thereto at a temperature of from −0.3 to 0.7° C. over a period of 10 minutes. Thereafter, an aqueous solution of 11.8 g (0.168 mols) of NaNO$_2$ and 100.1 g of H$_2$O was added thereto dropwise at a temperature of from −3.1 to −0.4° C. over a period of 10 minutes. After the dropwise addition has been finished, the reaction was conducted at a temperature of from −3.8 to 23.0° C. for 3 hours, and a 5,5'-bi-1H-tetrazolesilver salt precipitated from 399.68 g of the reaction solution was filtered to isolate 52.45 g of the wet 5,5'-bi-1H-tetrazolesilver salt.

52.45 Grams of the wet 5,5'-bi-1H-tetrazolesilver salt and 100.20 g of the H$_2$O were fed to a 200-ml distillation flask, and 18.4 g (0.077 mols) of Na$_2$S.9H$_2$O was added thereto in a slurry state at a temperature of from 45 to 48° C. over a period of 15 minutes. The reaction was further conducted at a temperature of from 50 to 52° C. for one hour. Ag$_2$S was separated from 170.51 g of the black slurry reaction solution and was washed with 40.4 g of H$_2$O followed by drying to recover 16.08 g of black crystalline Ag$_2$S [calculated amount 19.82 g, recovery rate 81.1%].

183.6 Grams of yellow separation motor liquor+washing water was condensed under a reduced pressure (~55° C., 60 mmHg). To 146.1 g of the condensed solution was added 8.4 g (0.155 mols) of 99.0% NH$_4$Cl, and the reaction was conducted at 50 to 55° C. for one hour.

After the reaction, the reaction solution was cooled, the precipitated crystals were separated, washed with 36.8 g of H$_2$O and was dried in a vacuum drier at a drying temperature of 50° C. for 8 hours to obtain 7.02 g of a 5,5'-bi-1H-tetrazolediammonium salt [BHT.2NH$_3$]. The amount of the separation mother liquor was 128.9 g and the amount of the washing solution was 41.6 g.

[Yield and analytical values of 5,5'-bi-1H-tetrazolediammonium salt [BHT.2NH$_3$]]Yield of coarse crystals: 48.7% on the basis of OAH Analytical values of coarse crystals: HClO$_4$tit. 95.56%, HPLC 97.56% (area %)

Comparative Example 3

Synthesis of 5,5'-bi-1H-tetrazolediammonium Salt [BHT.2NH$_3$]

10.07 Grams (0.081 mol) of 93.04% oxaldiimidic acid dihydrazide (OAH) and 100.0 g of H$_2$O were fed into a 500-ml distillation flask, and were cooled down to 5° C. in a slurry state. A mixed aqueous solution of 36.6 g (0.350 mols) of 35% HCl and 65.0 g of H$_2$O was added thereto dropwise at a temperature of from 2.4 to 8.1° C. over a period of 15 minutes. Accompanying the dropwise addition of HCl, the OAH crystals have dissolved, and the solution has changed into a yellow homogeneous solution.

Next, 12.8 g (0.182 mols) of 98.5% NaNO$_2$ and 90.1 g of H$_2$O were added thereto dropwise at a temperature of from −3.0 to 0.5° C. over a period of one hour and 10 minutes. After the dropwise addition has been finished, the reaction was conducted at a temperature of from −2.0 to 16.5° C. for one hour and, then, at 50° C. for 2 hours.

Thereafter, an aqueous solution of 13.8 g (0.341 mols) of NaOH and 20.0 g of H$_2$O was added thereto dropwise. The mixture was stirred at a temperature of 40° C. for 30 minutes to convert the 5,5'-bi-1H-tetrazole into a 5,5'-bi-1H-tetrazoledisodium salt.

After stirring, the insoluble components were filtered. To 344.3 g of the reaction solution was added 9.4 g (0.170 mols) of 99.0% $NH_4Cl$, and the 5,5'-bi-1H-tetrazoledisodium salt [BHT.2Na] was reacted with the $NH_4Cl$ at a temperature of 40° C. for 30 minutes to synthesize the 5,5'-bi-1H-tetrazolediammonium salt [BHT.2NH$_3$].

After the reaction, the reaction solution was condensed under a reduced pressure (−50° C., 25 mmHg). To 50.3 g of the condensed solution was added 100.0 g of $H_2O$. The mixture was stirred at a temperature of 35° C. for 30 minutes, followed by cooling down to 10° C. The precipitated crystals were separated and washed with 44.0 g of $H_2O$ to isolate 9.9 g of a yellow wet 5,5'-bi-1H-tetrazolediammonium salt [BHT.2NH$_3$] which was then dried in a vacuum drier at a drying temperature of 50° C. for 5 hours to obtain 4.2 g of a 5,5'-bi-1H-tetrazolediammonium salt [BHT.2NH$_3$]. The total amount of the separation mother liquor+washing solution was 187.2 g.

[Yield and analytical values of 5,5'-bi-1H-tetrazolediammonium salt [BHT.2NH$_3$]]Yield of coarse crystals: 28.4% on the basis of OAH Analytical values of coarse crystals: HPLC, 80.2% (area %)

Comparative Example 4

Synthesis of 5,5'-bi-1H-tetrazolediammonium Salt [BHT.2NH$_3$]

9.52 Grams (0.080 mol) of 97.59% oxaldiimidic acid dihydrazide (Example 1)(OAH) and 200.45 g of $H_2O$ were fed into a 500-ml distillation flask, and were cooled down to 10° C. in a slurry state. A mixed aqueous solution of 33.40 g (0.320 mols) of 60.35% $HNO_3$ and 33.81 g of $H_2O$ was added thereto dropwise at a temperature of from 0.1 to 9.9° C. over a period of 20 minutes. Accompanying the dropwise addition of $HNO_3$, the OAH crystals have dissolved, and the solution has changed into a faintly yellow homogeneous solution. Upon adding 12.82 g (0.160 mols) of 99.87% $NH_4NO_3$ at a temperature of from 1.2 to 12.0° C. over a period of 15 minutes, the faintly yellow homogeneous solution has changed into a white slurry.

Next, 11.21 g (0.160 mols) of 98.5% $NaNO_2$ and 50.01 g of $H_2O$ were added thereto dropwise at a temperature of from −3.8 to −1.5° C. over a period of 50 minutes. After the dropwise addition has been finished, the reaction was conducted at a temperature of from −6.5 to −1.5° C. for one hour.

Thereafter, 63.52 g (0.480 mols) of 30.24% NaOH aqueous solution was added thereto dropwise at a temperature of from −5.6 to −3.6° C. over a period of 15 minutes to convert the 5,5'-bi-1H-tetrazole into a 5,5'-bi-1H-tetrazoledisodium salt.

The reaction solution was heated at 50° C., 25.99 g (0.480 mols) of 99.0% $NH_4Cl$ and 38.91 g of $H_2O$ were added thereto dropwise at a temperature of from 51.1 to 52.2° C. over a period of 10 minutes, and the 5,5'-bi-1H-tetrazoledisodium salt [BHT.2Na] was reacted with the $NH_4Cl$ to synthesize a 5,5'-bi-1H-tetrazolediammonium salt [BHT.2NH$_3$].

After the dropwise addition of the $NH_4Cl$ solution has been finished, 566.88 g of the reaction solution was cooled down to −2° C., and the precipitated crystals were separated and washed with 26.0 g of $H_2O$ to isolate 6.90 g of the wet 5,5'-bi-1H-tetrazolediammonium salt (BHT.2NH$_3$) which was then dried in a vacuum drier at a drying temperature of 60° C. for 6 hours to obtain 3.02 g of a 5,5'-bi-1H-tetrazolediammonium salt [BHT.2NH$_3$]. The total amount of the separation mother liquor+washing solution was 580.24 g.

[Yield and analytical values of 5,5'-bi-1H-tetrazolediammonium salt [BHT.2NH$_3$]]Yield of coarse crystals: 20.1% on the basis of OAH Analytical values of coarse crystals: $HClO_4$tit. 91.65% HPLC, 91.58% (area %)

According to the present invention, hydrazine hydrate is reacted with dicyan, oxaldiimidic acid dihydrazide (OAH) of a high purity quantitatively obtained via 1-cyanoformimidic acid hydrazide (CFAH) is dissolved in an aqueous solution of a weakly acidic compound such as acetic acid and to which is dropwisely added an aqueous solution of sodium nitrite to form an azide thereof and to effect the cyclization reaction by heating. To the reaction product is then added an aqueous solution of sodium hydroxide to convert the product into a 5,5'-bi-1H-tetrazoledisodium salt (BHT.2Na) which is then reacted with an aqueous solution of ammonium chloride, and the formed ammonium salt is recovered as sparingly soluble crystals, in order to obtain a 5,5'-bi-1H-tetrazolediammonium salt (BHT.2NH$_3$) from the starting materials which are cheaply available and are easy to handle, without requiring cumbersome after-treatment yet maintaining a high yield.

The invention claimed is:

1. A process for the preparation of 5,5'-bi-1H-tetrazolediammonium salts, wherein oxalimidic acid dihydrazide is reacted with sodium nitrite in the presence of an acidic substance while maintaining the pH of the reaction solution in a range of from 4 to 6 to form 5,5'-bi-1H-tetrazole through the formation of an azide thereof, and the 5,5'-bi-1H-tetrazole is converted into 5,5'-bi-1H-tetrazoledisodium salt by the addition of sodium hydroxide, the 5,5'-bi-1H-tetrazoledisodium salt is further reacted with ammonium chloride or an aqueous solution thereof, and a formed ammonium salt is recovered as sparingly soluble crystals.

2. A preparation process according to claim 1, wherein there is added a weakly acidic compound having a pKa of 3 to 5, such as formic acid, acetic acid, propionic acid, octanoic acid or citric acid.

3. A preparation process according to claim 1, wherein an aqueous solution of sodium nitrite is dropwisely added at −10 to 30° C., an azide thereof is formed and a cyclization reaction is conducted at 10 to 70° C. for 1 to 7 hours.

4. A preparation process according to claim 1, wherein an aqueous solution of sodium hydroxide is added to said reaction solution, and the reaction is conducted at 20 to 90° C. for 1 to 5 hours to synthesize a 5,5'-bi-1H-tetrazoledisodium salt.

5. A preparation process according to claim 1, wherein ammonium chloride or an aqueous solution thereof is added to said reaction solution at 30 to 90° C., and the reaction is conducted at 50 to 90° C. for 1 to 3 hours to synthesize a 5,5'-bi-1H-tetrazoledisodium salt.

6. A preparation process according to claim 1, wherein a weakly acidic compound is so added that a molar ratio (B/A) of the weakly acidic compound (B) to the oxaldiimidic acid dihydrazide (A) is from 2.0 to 4.0.

7. A preparation process according to claim 1, wherein the sodium nitrite is so added that a molar ratio (C/A) of the sodium nitrite (C) to the oxaldiimidic acid dihydrazide (A) is from 2.0 to 4.0.

8. A preparation process according to claim 1, wherein the sodium hydroxide is so added that a molar ratio (D/A) of the sodium hydroxide (D) to the oxaldiimidic acid dihydrazide (A) is from 2.0 to 3.5.

9. A preparation process according to claim 1, wherein the ammonium chloride is so added that a molar ratio (E/A) of the ammonium chloride (E) to the oxaldiimidic acid dihydrazide (A) is from 2.0 to 3.5.

10. The process of claim 1, wherein the oxaldiimidic acid dihydrazide is prepared from dicyan and hydrazine hydrate of an amount larger than a stoichiometric ratio thereof to the dicyan.

11. the process according to claim 10, wherein the reaction of dicyan and hydrazine hydrate is conducted at −10 to 50° for 2 to 30 hours and, after the reaction, the precipitated crystals are separated.

12. The process according to claim 10, wherein the reaction of dicyan to hydrazine hydrate is conducted at a molar ratio (G/F) of the hydrazine hydrate (G) to the dicyan (F) of from 2.5 to 3.5.

13. The process according to claim 10, wherein a polar solvent such as water, alcohol, or a mixed solvent thereof is used as the reaction solvent.

* * * * *